United States Patent [19]

Idriss et al.

[11] Patent Number: 5,841,012
[45] Date of Patent: Nov. 24, 1998

[54] HYDROGENATION CATALYSTS FOR LOW CONCENTRATION OF CHLOROPRENE AND TRICHLOROETHYLENE IN ETHANE DICHLORIDE STREAM

[75] Inventors: Hicham Idriss, Auckland, New Zealand; Adbulrahman Saleh Al-Ubaid, Riyadh, Saudi Arabia; Saeed Mohammed Al-Wahabi, Riyadh, Saudi Arabia; Khalid El Yahyaoui, Riyadh, Saudi Arabia

[73] Assignee: Saudi Basic Industries Corporation, Saudi Arabia

[21] Appl. No.: 778,307

[22] Filed: Jan. 2, 1997

[51] Int. Cl.$^6$ ............... C07C 5/03; B01J 21/08
[52] U.S. Cl. ............ 585/260; 502/242; 585/274; 585/276
[58] Field of Search ............... 585/260, 274, 585/276; 502/242

[56] References Cited

U.S. PATENT DOCUMENTS

| | | | |
|---|---|---|---|
| 3,591,656 | 7/1971 | Kroll et al. | 260/683.9 |
| 4,145,367 | 3/1979 | Boozalis et al. | 260/652 |
| 4,929,781 | 5/1990 | James Jr. et al. | 585/310 |

*Primary Examiner*—Alan L. Rotman
*Assistant Examiner*—Charanjit S. Aulakm
*Attorney, Agent, or Firm*—Whitman, Breed, Abbott & Morgan LLP; William J. Spatz, Esq.; John E. Boyd, Esq.

[57] ABSTRACT

High space velocity catalysts useful in the substantial elimination of chloroprene and trichloroethylene from an industrial product stream of ethane dichloride; the last is useful in the production of vinyl chloride.

20 Claims, No Drawings

HYDROGENATION CATALYSTS FOR LOW CONCENTRATION OF CHLOROPRENE AND TRICHLOROETHYLENE IN ETHANE DICHLORIDE STREAM

FIELD OF THE INVENTION

The present invention relates to catalysts and methods for hydrogenation of chlorinated, double-bonded hydrocarbons in low concentration. In particular, the present invention relates to total or substantially total hydrogenation of chloroprene (2-chloro-1,3-butadiene) as well as substantial hydrogenation of trichloroethylene which are present in small amounts (up to 4000 ppm) in effluent from an ethane dichloride industrial reaction unit without affecting in a recognizable manner the ethane dichloride product. Thus, ethane dichloride is not decomposed during this hydrogenation.

BACKGROUND OF THE INVENTION

U.S. Pat. No. 4,145,367 describes Pd catalysts deposited on inert supports, namely $SiO_2$ and charcoal. Complete hydrogenation of double bonded chlorinated hydrocarbons on 1 wt. % $Pd/SiO_2$ is described when the reactor volume is 300 ml and the recycle rate of 1,2-dichloroethane is 191 ml/hour (that is, with a space velocity of $0.637H^{-1}$) and when the chloroprene concentration is equal to 0.6% (or 600 ppm).

It is also described in U.S. Pat. No. 4,145,367 that chloroprene and trichloroethane are "completely" hydrogenated on 0.5 wt. % Pd/charcoal when the catalyst volume is 100 ml and the recycle rate of 1,2-dichloroethane is 200 ml/hour (or with a space velocity of $2H^{-1}$) and when the chloroprene concentration is equal to 0.01% (or 1 ppm) and the trichloroethane concentration is equal to 4.33% (or 4340 ppm).

The space velocity of $2H^{-1}$ calculated from U.S. Pat. No. 4,145,367 is relatively slow and it would be highly advantageous to use a catalyst which hydrogenates chloroprene with higher space velocities.

In addition, it is also desired to hydrogenate trichloroethylene since this later unwanted by-product might also polymerize as previously indicated in U.S. Pat. No. 4,145,367.

In another work (Chem. Zvesti 26, 466 (1972)) the authors described complete hydrogenation as well as hydrodechlorination of chloroprene on $Rh/Al_2O_3$ catalysts, although they did not study the hydrogenation reaction in the presence of ethane dichloride.

It is also known that the hydrogenation reaction of olefins (such as ethylene) on Pt is a structure sensitive reaction (J. Phys. Chem. 94, 5300 (1990)) and that very small Pd particles (diameter=10–40 Å) are less active towards the hydrogenation than larger Pd particles (diameter>40 Å) (Catal. Lett. 22, 197 (1993)).

It is known that the addition of alkalis to Pd (in very small amount) increases the rate of hydrogenation of ethylene (J. Phys. Chem. 95, 7368 (1991)) and increases the noble metal dispersion (Appl. Catal. 51, 165 (1989)) and that Co is further reduced when present with Pd when supported on $CeO_2$ (New Frontiers in Catalysis, p. 2119, Elsevier (1993)). It is also well known that metals such as Pd and Pt have a strong interaction with some oxides such as $TiO_2$ (J. Catal. 55, 29 (1978) and J. Am. Chem. Soc. 100, 170 (1978)).

Each publication identified above and those referred to hereinafter are hereby incorporated by reference.

It is therefore desired by this invention to provide a catalyst and method for hydrogenation of chlorinated double-bonded hydrocarbons in low concentration dispersed in dichloroethane.

It is further desired by this invention to provide a catalyst and method for hydrogenation of chloroprene as well as trichloroethylene which are present in small amounts in effluent from an ethane dichloride industrial reaction unit and to provide such a catalyst and method which hydrogenates chloroprene with high space velocities.

SUMMARY OF THE INVENTION

The present invention deals with total or partial hydrogenation and/or extinction hydrogenation of chloroprene (CP, 2-chloro-1,3-butadiene) as well as substantial or i.e. near extinction hydrogenation of trichloroethylene (TCE) which are present in small amounts (up to 4000 ppm) in effluent from an ethane dichloride (EDC) industrial reaction unit. Ethane dichloride to the best of our knowledge is not decomposed or affected during this hydrogenation.

To provide more environmentally desirable process and to avoid undesirable process consequences when these impurities are present, (e.g. polymerization of the impurities in plant reactors), the present invention is directed to the hydrogenation of double bonds of CP rather than chlorination. In the manufacture of ethane dichloride from ethylene, where the former is used for the production of vinyl chloride monomers (VCM), a number of by-products are formed, the most annoying of which is chloroprene. Presently the double bonds of chloroprene are chlorinated. The chlorination step is essential since chloroprene tends to polymerize and causes major inconveniences in process equipment because of its polymerization. However, it is highly recommended to substitute the chlorination step because of environmental issues. The present invention addresses the possibility of hydrogenating chloroprene, in such conditions where ethane dichloride is not decomposed, i.e. without breaking the C—Cl bonds.

Desirable, high space velocity hydrogenation reactions occurred on Pd or Pt deposited on one or a mixture of the following oxides: $TiO_2$, $La_2O_3$, $V_2O_5$, $CeO_2$, and $ZrO_2$, non-supported or supported on $Al_2O_3$, $SiO_2$ or activated carbon. Alkalis, such as Li, Na, and K, may or are advantageously used as promoters. In addition the hydrogenation activity of the Pd or Pt catalysts is advantageously increased by addition of non noble metals, such as Co or Ni.

The catalyst formulation of the present invention is as follows:

MXYZ wherein

M=Pd, Pt 0.01 to 5% (wt %)

X=Li, Na, K, Co, Ni 0 to 3% (wt %)

Y=$TiO_2$, $La_2O_3$, $V_2O_5$, $CeO_2$l $ZrO_2$ 0 to 99.9% (wt %)

Z=$Al_2O_3$, $SiO_2$, Activated Carbon 0 to 95% (wt %).

Components Y and Z as "supports" may also be used in a "balance" relationship, i.e. Y of a given percent, balance Z.

The present invention also addresses the preparation of Pd and Pt catalysts with an appropriate metal particle diameter in order to find the most suitable catalyst for the hydrogenation of chlorinated double bonded hydrocarbons. The method for determination of the particle diameter used in the present invention is Co adsorption (a pulse method) (Anderson, J. R. and Pratt, K. C. "Introduction to Characterization and Testing of Catalysts", Academic Press (1982)), which is still very useful for comparing metal particle size (Satterfield, C. N. "Heterogeneous Catalysis in Industrial Practice", McGraw-Hill, Inc., (1991)).

The present invention is directed mainly to the Pd and Pt catalysts; on supports such as $TiO_2$, $La_2O_3$, $V_2O_5$, $CeO_2$, and $ZrO_2$; in the presence or absence of alkalis such as Li, Na, or K desirably in the presence of these, and optionally with co-impregnated Co or Ni but desirably in the presence of these as well. As indicated above, in some cases $Al_2O_3$, $SiO_2$ or activated carbon was used as support together with an oxide such as $TiO_2$, $La_2O_3$, $V_2O_5$, $CeO_2$ and $ZrO_2$ with the Pd or Pt.

Accordingly, the present invention is directed to total or substantially total hydrogenation of chloroprene as well as substantial hydrogenation of trichloroethylene in ethane dichloride feed. The chloroprene and trichloroethylene are each present with concentrations of up to 4000 ppm. All catalysts presented in this invention were able to completely hydrogenate chloroprene in this range of concentration without detectable decomposition of ethane dichloride. The percentage of conversion, i.e. degree of exhaustion or extinction depends on the space velocities used for the liquid containing ethane dichloride, chloroprene and trichloroethylene. It is desired to substantially entirely convert in a single pass the entire impurity load in the stream at the highest space velocity (expressed as $H^{-1}$). One skilled in the art will appreciate that other impurities are present in addition to chloroprene and trichloroethylene in the reaction feed, such as benzene and/or dichloromethane.

DETAILED DESCRIPTION OF THE INVENTION

Catalyst Preparation

Catalysts were prepared by impregnation of the noble metal Pd or Pt from their salts (preferably nitrates and chlorides) on the support. The support was either used as purchased in the form of oxide or precipitated from its nitrate, such as in the case of cerium oxide precipitated from cerium nitrate using ammonia at pH 8. In the case of co-impregnation of the noble metal with Co or Ni, metal nitrate was used as precursor. After complete impregnation, catalysts were dried at 120° C. overnight then calcined in air at a temperature between 300° C. and 500° C. for 5 to 10 hours. Preferably, before starting the reaction the catalyst is reduced in hydrogen at temperatures between 150° C. and 400° C. for a period between 2 hours and 24 hours depending on the support used.

Metal particle dimensions were obtained by CO adsorption (pulse method) in a quartz reactor. All catalysts (0.5 g), prior to CO adsorption (at room temperature), were reduced at 250° C. for four hours or more in the presence of hydrogen. The amount of adsorbed CO per gram of catalyst was between $10^{17}$ and $10^{19}$ molecules of CO depending on the type of catalysts.

Catalytic Reaction

The catalytic reaction was done in stainless steel fixed bed reactors of internal diameter of 0.6 and 1.0 cm. Hydrogen was mixed with the actual industrial feed which contained 96–98% ethane dichloride together with chloroprene, trichloroethylene and other contaminants. In all experiments the amount of hydrogen exceeded by at least 300% the stoichiometric ratio required to achieve complete hydrogenation of all unsaturated contaminants. Total amount of contaminants is obtainable for each product pass from a gas chromatography method or the like. The liquid containing ethane dichloride plus the converted chloroprene and trichloroethylene was trapped at the outlet of the reactor in an ice bath. The trapped liquid was analyzed using gas chromatography. Chloroprene conversion and trichloroethylene conversion were monitored by the disappearance of the chloroprene and trichloroethylene peaks related to an internal standard (dichloromethane).

The above reaction temperature was between 120° C. and 250° C., preferably between 140° C. and 200° C., to assure no decomposition of ethane dichloride. The reaction pressure was between 1 and 10 atm.

The present invention is further described and illustrated in the following examples. Further desirable aspects of this invention, together with additional features contributing thereto and advantages accruing therefrom, will be apparent from the following examples of the invention.

It will be appreciated that variations and modifications to the products and methods can be made by the skilled person as prescribed by the Examples. These examples are not to be construed as limiting the invention but rather as illustrations of the invention.

EXAMPLE 1

Catalyst 0.5 wt % Pd-0.3 wt % $Co/TiO_2$

A 0.5 wt % Pd-0.3 wt % $Co/TiO_2$ catalyst was prepared and tested as follows:

1.66 g of $PdCl_2$ was dissolved in 500 ml 1N HCl solution by stirring for 12 hours at room temperature (solution A).

25 ml of solution A was added to 10 g of $TiO_2$ and 120 mg of cobaltous chloride hexahydrate to give mixture B.

The obtained mixture B was stirred under mild heating (100° C.) for 5 hours or until paste formation.

The paste obtained in step C was calcined at 350° C. under air for 5 hours. The obtained catalyst had a surface area of 11.4 $m^2/g$ and could absorb $1.97 \times 10^{18}$ molecules of CO/g at room temperature.

2 g of the catalyst were loaded in a 0.6 cm (internal diameter) stainless steel reactor and were reduced for 12 hours under 10 ml/min hydrogen at 200° C. and 1.0 atm.

The temperature of the catalyst was decreased to 170° C. and the hydrogen pressure was kept at 2.0 atm.

Industrial stream containing of ethane dichloride (96+% EDC+CP+TCE) at a space velocity of $2H^{-1}$ was mixed with hydrogen (hydrogen space velocity=$600H^{-1}$) at the top of the reactor. At the outlet of the reactor the liquid was trapped in ice bath.

After periods between 0.5 hours and 1.5 hours the reaction was stopped and the liquid was analyzed. 100% conversion of chloroprene and 95+% conversion of trichloroethylene were obtained per single pass of the product. No sign of catalyst deactivation was observed after 50 hours at the working conditions.

EXAMPLE 2

Catalyst 0.28 wt. % $Pt/V_2O_5$

A catalyst 0.28 wt. % $Pt/V_2O_5$ was prepared and tested as in Example 1 and had a surface area of 77.5 $m^2/g$ and a particle diameter of 12.6 Å.

At a reaction temperature of 150° C., a pressure of 3.5 atm., hydrogen space velocity of $240H^{-1}$, and liquid space velocity of $3.5H^{-1}$, the chloroprene conversion was 92.5% and the trichloroethylene conversion was 64% per one pass of the product.

EXAMPLE 3

Catalyst 0.1 wt. % $Pt/TiO_2$

Catalyst 0.1 wt. % $Pt/TiO_2$ was prepared and tested as in Example 1.

At a reaction temperature of 130° C., a pressure of 3.0 atm., hydrogen space velocity of $240H^{-1}$ and liquid space velocity of $0.27H^{-1}$, the chloroprene conversion was 92.0% and the trichloroethylene conversion was 24.5% per single pass of the product.

EXAMPLE 4

Catalyst 0.1 wt. % $Pt/La_2O_3$

Catalyst 0.1 wt. % $Pt/La_2O_3$ was prepared and tested as in Example 1 and had a surface area of 12.5 $m^2/g$.

At a reaction temperature of 160° C., a pressure of 2.7 atm., a hydrogen space velocity of 1700H$^{-1}$, and liquid space velocity of 5.8H$^{-1}$, the chloroprene conversion was 90.0% and the trichloroethylene conversion was 45% per single pass of the product.

EXAMPLE 5

Catalyst 0.4 wt. % Pt/La$_2$O$_3$

Catalyst 0.4 wt. % Pt/La$_2$O$_3$ was prepared and tested as in Example 1 and had a metal particle diameter of 82.5 Å.

At a reaction temperature of 160° C., a pressure of 3.0 atm., hydrogen space velocity of 456H$^{-1}$ and liquid space velocity of 6.0H$^{-1}$, the chloroprene conversion was 92.0% and the trichloroethylene conversion was 78% per single pass of the product.

EXAMPLE 6

Catalyst 0.4 wt. % Pt/TiO$_2$

Catalyst 0.4 wt. % Pt/TiO$_2$ was prepared and tested as in Example 1 and had a surface area of 68 m$^2$/g and metal particle diameter of 84 Å.

At a reaction temperature of 165° C., a pressure of 3.0 atm., hydrogen space velocity of 240H$^{-1}$, and liquid space velocity of 4.18H$^{-1}$, the chloroprene conversion was 100% and the trichloroethylene conversion was 34% per single pass of the product.

EXAMPLE 7

Catalyst 0.5 wt % Pd/TiO$_2$

Catalyst 0.5 wt % Pd/TiO$_2$ was prepared and tested as in Example 1 and had a surface area of 7 m$^2$/g and metal particle diameter of 250 Å.

At a reaction temperature of 160° C., a pressure of 2.0 atm., a hydrogen space velocity of 720H$^{-1}$, and liquid space velocity of 4.1H$^{-1}$, the chloroprene conversion was 100% and the trichloroethylene conversion was 78% per single pass of the product.

EXAMPLE 8

Catalyst 0.5 wt. % Pd/La$_2$O$_3$

Catalyst 0.5 wt. % Pd/La$_2$O$_3$ was prepared and tested as in Example 1 and had a surface area of 19.5 m$^2$/g and metal particle diameter of 400 Å.

At a reaction temperature of 160° C., a pressure of 2.5 atm., a hydrogen space velocity of 2400H$^{-1}$, and liquid space velocity of 4.0H$^{-1}$, the chloroprene conversion was 100% and the trichloroethylene conversion was 44% per single pass of the product.

EXAMPLE 9

Catalyst 0.5 wt. % Pd-0.2 wt. % Na/TiO$_2$

Catalyst 0.5 wt. % Pd-0.2 wt. % Na/TiO$_2$ was prepared and tested as in Example 1 and had a surface area of 8.7 m$^2$/g and metal particle diameter of 1350 Å.

At a reaction temperature of 160° C., a pressure of 2.5 atm., hydrogen space velocity of 1200H$^{-1}$, and liquid space velocity of 3.8H$^{-1}$, the chloroprene conversion was 85% and the trichloroethylene conversion was 20% per single pass of the product.

EXAMPLE 10

Catalyst 0.5 wt. % Pd-0.3 wt. % Co/TiO$_2$

Catalyst 0.5 wt. % Pd-0.3 wt. % Co/TiO$_2$ was prepared and tested as in Example 1 and had a surface area of 11.4 m$^2$/g and metal particle diameter of 295 Å.

At a reaction temperature of 170° C., a pressure of 2.0 atm., hydrogen space velocity of 600H$^{-1}$ and a liquid space velocity of 2H$^{-1}$, the chloroprene conversion was 100% and the trichloroethylene conversion was 95% per single pass of the product.

EXAMPLE 11

Catalyst as in example 10

At a reaction temperature of 170° C., a pressure of 2.0 atm., a hydrogen space velocity of 600H$^{-1}$ and a liquid space velocity of 10.7H$^{-1}$, the chloroprene conversion was 100% and the trichloroethylene conversion was 25% per single pass of the product.

EXAMPLE 12

Catalyst 0.5 wt. % Pd/Activated carbon

Catalyst 0.5 wt. % Pd/Activated carbon was prepared and tested as in Example 1 and had a surface area of 1000 m$^2$/g and metal particle diameter of 44 Å.

At a reaction temperature of 170° C., a pressure of 2 atm., hydrogen space velocity of 600H$^{-1}$, and liquid space velocity of 5H$^{-1}$, the chloroprene conversion was 100% and the trichloroethylene conversion was 62% per single pass of the product.

EXAMPLE 13

Catalyst 0.5 wt. % Pd-5 wt. % TiO$_2$/Alumina

Catalyst 0.5 wt. % Pd-5 wt. % TiO$_2$ balance alumina was prepared and tested as in Example 1 and had a surface area of 176 m$^2$/g and metal particle diameter of 26 Å.

At a reaction temperature of 170° C., a pressure of 2 atm., hydrogen space velocity of 600H$^{-1}$, and liquid space velocity of 27H$^{-1}$, the chloroprene conversion was 100% and the trichloroethylene conversion was 42% per single pass of the product.

EXAMPLE 14

Catalyst 3 wt. % Pd/CeO$_2$

Catalyst 3 wt. % Pd/CeO$_2$ was prepared and tested as in Example 1 and had a surface area of 38.4 m$^2$/g.

At a reaction temperature of 170° C., a pressure of 2 atm., hydrogen space velocity of 600H$^{-1}$, and liquid space velocity of 0.97H$^{-1}$, the chloroprene conversion was 90.2% per single pass of the product.

EXAMPLE 15

Catalyst 0.5 wt. % Pd/0.2 wt. % Li/TiO$_2$

Catalyst 0.5 wt. % Pd/0.2 wt. % Li/Tio$_2$ was prepared and tested as in Example 1 and had a surface area of 0.56 m$^2$/g and metal particle diameter of 993 Å.

At a reaction temperature of 170° C., a pressure of 2 atm., hydrogen space velocity of 600H$^{-1}$, and liquid space velocity of 0.22H$^{-1}$, the chloroprene conversion was 68% per single pass of the product.

EXAMPLE 16

Catalyst 0.3 wt. % Pd/0.5 wt. % Ni/TiO$_2$

Catalyst 0.3 wt. % Pd/0.5 wt. % Ni/TiO$_2$ was prepared and tested as in Example 1 and had a surface area of 9.73 m$^2$/g and metal particle diameter of 1200 Å.

At a reaction temperature of 170° C., a pressure of 2 atm., hydrogen space velocity of 600H$^{-1}$, and liquid space velocity of 0.18H$^{-1}$, the chloroprene conversion was 85% per single pass of the product.

EXAMPLE 17

Catalyst 0.5 wt. % Pd/ZrO$_2$

Catalyst 0.5 wt. % Pd/ZrO$_2$ was prepared and tested as in Example 1 and had a surface area of 0.54 m$^2$/g and metal particle diameter of 1040 Å.

At a reaction temperature of 170° C., a pressure of 2 atm., hydrogen space velocity of 600H$^{-1}$, and liquid space velocity of 5H$^{-1}$, the chloroprene conversion was 100% per single pass of the product.

EXAMPLE 18

Catalyst 0.5 wt. % Pd/SiO$_2$

Catalyst 0.5 wt. % Pd/SiO$_2$ was prepared and tested as in Example 1 and had a surface area of 93.3 m$^2$/g and metal particle diameter of 370 Å.

At a reaction temperature of 170° C., a pressure of 2 atm., hydrogen space velocity of 600H$^{-1}$, and liquid space velocity of 0.17H$^{-1}$, the chloroprene conversion was 99% per single pass of the product.

EXAMPLE 19

Catalyst 0.5 wt. % Pd-0.2 wt. % K/TiO$_2$

Catalyst 0.5 wt. % Pd-0.2 wt. % K/TiO$_2$ was prepared and tested as in Example 1 and had a surface area of 9.01 m$^2$/g and metal particle diameter of 1304 Å.

At a reaction temperature of 170° C., a pressure of 2 atm., hydrogen space velocity of 600H$^{-1}$, and liquid space velocity of 0.31H$^{-1}$, the chloroprene conversion was 65% per single pass of the product.

EXAMPLES 20 and 21

Comparative Testing Between the Catalysts of the Present Invention and those of U.S. Pat. No. 4.145,367

Wherever in the above examples "catalyst/support" has been so indicated, the support is "balance" based on weight percent of the composition.

While U.S. Pat. No. 4,145,367 indicated that Pt is too slow for industrial use, as best illustrated by Example 5, it has been found that Pt, when deposited on the appropriate support where a metal-support interaction occurs, can be nearly as good as Pd for the hydrogenation of chloroprene.

Based on the above described reactions and examples, complete exhaustion of chloroprene is achievable with a number of catalysts per single pass of the product over the catalyst at desirably high space velocity of at least above 0.17H$^{-1}$. Conventional wisdom is that at lower space velocities higher conversion is achieved. However, the present examples indicate that at high space velocities (not only for previously less active and less desirable catalysts such as platinum) highly desired results will be achieved. Moreover, catalysts appropriately modified, show high space velocities with complete conversion, i.e. extinction, of the undesired product. However, the catalyst of the invention can be used at higher space velocity with less conversion. Total, or near total, conversion can be achieved to lead to complete, or substantially complete, extinction of the undesired product (s) by subjecting the catalytic reaction product to two or more passes through the reactor, or additional reactors, or by recycling a portion of the catalytic reaction product.

As seen from the above, not only is the space velocity enhanced by the catalytic function of component X, but it also appears that the support functions in some manner as a catalytic action enhancer (cf. Example 21) completely unexpected based on space velocity basis.

These high space velocities as illustrated in the examples indicate the following characteristics for the derived or preferred catalytic composition: particle size up to 13500 Å, preferably from 10 Å to 500 Å; base support desirably of Alumina, Silica or Activated Carbon and preferably of a combination of TiO$_2$ with Alumina; as component X in the catalyst Na of alkali metals and Co of Co or Ni group of additives; and as component Z Alumina and Silica, preferably Alumina.

As it is also indicated and evident from the above comparisons, the outstanding space velocities provide for excellent industrial application of the present catalysts and important improvements in the space time yields along with the elimination of environmentally undesirable reactions.

What is claimed is:

1. A catalyst of the formula MXYZ for hydrogenation of chloroprene and trichloroethylene present in an ethane dichloride product stream, wherein M is 0.01 to 5 wt. % of a metal selected from the group consisting of Pd, Pt and mixtures thereof;

|  | EXAMPLE 20 | | EXAMPLE 21 | |
| --- | --- | --- | --- | --- |
|  | U.S. PAT. NO. 4,145,367 | PRESENT INVENTION | U.S. PAT. NO. 4,145,367 | PRESENT INVENTION |
| CATALYST USED | 1% Pd/SiO$_2$ | 0.5% Pd-0.3% Co/TiO$_2$ | 0.5% Pd/Charcoal | 0.5% Pd-5% TiO$_2$/balance Al$_2$O$_3$ |
| CP Conversion, % | 100 | 100 | 100 | 100 |
| Space Velocity, H$^{-1}$ | 0.6 | 10.7 | 2.0 | 27.0 |

X is 0.2 to 3 wt. % of an element selected from the group consisting of Li, Na, K, Co, Ni and mixtures thereof;

Y is 0 to 99.9 wt. % of an oxide selected from the group consisting of $TiO_2$, $La_2O_3$, $V_2O_5$, $CeO_2$, $ZrO_2$ and mixtures thereof; and Z is 0 to 95 wt. % of a support selected from the group consisting of $Al_2O_3$, $SiO_2$, activated carbon and mixtures thereof.

2. The catalyst as claimed in claim 1, wherein the amount of metal M is 0.1 to 4 wt. %.

3. The catalyst as claimed in claim 1, wherein the amount of metal M is 0.4 to 3 wt. %.

4. A method for hydrogenation of chloroprene and trichloroethylene present in an ethane dichloride product stream, which comprises contacting the product stream with hydrogen and a catalyst of the formula MXYZ, wherein M is 0.01 to 5 wt. % of a metal selected from the group consisting of Pd, Pt and mixtures thereof;

X is 0.2 to 3 wt. % of an element selected from the group consisting of Li, Na, K, Co, Ni and mixtures thereof;

Y is 0 to 99.9 wt. % of an oxide selected from the group consisting of $TiO_2$, $La_2O_3$, $V_2O_5$, $CeO_2$, $ZrO_2$ and mixtures thereof; and Z is 0 to 95 wt. % of a support selected from the group consisting of $Al_2O_3$, $SiO_2$, activated carbon and mixtures thereof and wherein Y, Z, or Y and Z is the residue balance of catalyst MX.

5. The method as claimed in claim 4, wherein the effluent, hydrogen and catalyst are contacted at a liquid space velocity of 0.1 to $50H^{-1}$ and at a hydrogen space velocity of 200 to $4,000H^{-1}$.

6. The method as claimed in claim 4, wherein the effluent, hydrogen and catalyst are contacted at a temperature of 100° to 250° C.

7. The method as claimed in claim 4, wherein the effluent, hydrogen and catalyst are contacted at a pressure of 1 to 10 atmospheres.

8. The method as claimed in claim 4, wherein the amount of metal M is 0.1 to 4 wt. %.

9. The method as claimed in claim 4, wherein the amount of metal M is 0.4 to 3 wt. %.

10. The method as claimed in claim 8, wherein M is Pd.

11. In a method for reducing the deleterious effects of chloroprene and trichloroethylene in the production of dichloroethane, the improvement comprising passing at a space velocity of greater than $0.1H^{-1}$, a dichloroethane product stream comprising said chloroprene and trichloroethylene over a catalyst as defined in claim 1.

12. The method as claimed in claim 11, wherein the product produced by passing said dichloroethane product stream over said catalyst is passed over a second catalyst as defined in claim 1 at a space velocity greater than $0.1H^{-1}$.

13. The method as claimed in claim 11, wherein a portion of the product produced by passing said dichloroethane product stream over said catalyst is recycled and mixed with said dichloroethane product stream prior to its being passed over said catalyst.

14. The catalyst of claim 1, wherein the catalyst has a particle size up to 1350 Angstrom.

15. The catalyst of claim 1, wherein the catalyst has a particle size from 10 to 500 Angstrom.

16. The method of claim 4, wherein the catalyst has a particle size up to 1350 Angstrom.

17. The method of claim 4, wherein the catalyst has a particle size from 10 to 500 Angstrom.

18. The method of claim 4, wherein said effluent, hydrogen and catalyst are contacted at a liquid space velocity greater than $2H^{-1}$ and at a hydrogen space velocity greater than $200H^{-1}$.

19. The method of claim 4, wherein said effluent, hydrogen and catalyst are contacted at a liquid space velocity greater than $3.5H^{-1}$ and at a hydrogen space velocity greater than $456H^{-1}$.

20. The method of claim 18, wherein the chloroprene conversion is greater than 90% per single pass of the product.

* * * * *